(12) United States Patent
Babu et al.

(10) Patent No.: US 8,470,608 B2
(45) Date of Patent: Jun. 25, 2013

(54) COMBINED VISUAL/FLUORESCENCE ANALYTE DETECTION TEST

(75) Inventors: Uma Mahesh Babu, Bradenton, FL (US); Robert W. VanDine, Montoursville, PA (US); Robert P. Sambursky, Bradenton, FL (US); Ganga Kanaujia, Bradenton, FL (US); Richard Rivas, Jr., Apollo Beach, FL (US)

(73) Assignee: Rapid Pathogen Screening, Inc, Sarasota, FL (US)

( * ) Notice: Subject to any disclaimer, the term of this patent is extended or adjusted under 35 U.S.C. 154(b) by 737 days.

(21) Appl. No.: 12/481,631

(22) Filed: Jun. 10, 2009

(65) Prior Publication Data

US 2009/0289201 A1    Nov. 26, 2009

Related U.S. Application Data

(63) Continuation-in-part of application No. 12/469,207, filed on May 20, 2009.

(60) Provisional application No. 61/060,258, filed on Jun. 10, 2008, provisional application No. 61/080,879, filed on Jul. 15, 2008, provisional application No. 61/098,935, filed on Sep. 22, 2008, provisional application No. 61/179,059, filed on May 18, 2009, provisional application No. 61/071,833, filed on May 20, 2008.

(51) Int. Cl.
    *G01N 33/558*    (2006.01)

(52) U.S. Cl.
    USPC ........... 436/514; 422/401; 422/420; 422/425; 435/287.7; 435/287.9; 435/805; 435/810; 435/970

(58) Field of Classification Search
    None
    See application file for complete search history.

(56) References Cited

U.S. PATENT DOCUMENTS

| 4,508,892 A   | 4/1985 | Yoshida |
| 4,859,612 A * | 8/1989 | Cole et al. ..................... 436/523 |
| 5,637,469 A   | 6/1997 | Wilding et al. |

(Continued)

FOREIGN PATENT DOCUMENTS

| DE | 19622503 C2 | 7/1998 |
| EP | 0306772 A1  | 3/1989 |

(Continued)

OTHER PUBLICATIONS

Uchio, et al., "Rapid Diagnosis of Adenoviral Conjunctivitis on Conjunctival Swabs by 10-Minute Immunochromatography," vol. 104, No. 8, Aug. 1997, pp. 1294-1299.

(Continued)

*Primary Examiner* — Chris L Chin
(74) *Attorney, Agent, or Firm* — Brown & Michaels, PC

(57) ABSTRACT

The sensitivity of visually read lateral flow immunoassay tests is enhanced by adding a small quantity of fluorescing dye or fluorescing latex bead conjugates to the initial conjugate material. When the visible spectrum test line is visibly present, the test result is observed and recorded. However, in the case where the result is indeterminate, a light of an appropriate spectrum, such as a UV, visible, or infrared spectrum, is cast on the test line to excite and fluoresce the fluorescing latex beads which are bound in the test line in true positive tests to enhance the visible color at the test line.

19 Claims, 8 Drawing Sheets

1: absorbant pad
2: sample application zone
3: detection zone
4: waste pad
5: carrier backing

U.S. PATENT DOCUMENTS

| | | | |
|---|---|---|---|
| 5,658,751 | A | 8/1997 | Yue et al. |
| 5,714,341 | A | 2/1998 | Thieme et al. |
| 6,037,127 | A | 3/2000 | Ebersole et al. |
| 6,087,088 | A | 7/2000 | Piran et al. |
| 6,136,610 | A * | 10/2000 | Polito et al. .................... 436/514 |
| 6,225,046 | B1 | 5/2001 | Vesey et al. |
| 6,335,205 | B1 | 1/2002 | Bausback |
| 6,514,773 | B1 | 2/2003 | Klein et al. |
| 6,569,627 | B2 | 5/2003 | Wittwer et al. |
| 6,875,619 | B2 | 4/2005 | Blackburn |
| 6,902,900 | B2 | 6/2005 | Davies et al. |
| 7,189,522 | B2 | 3/2007 | Esfandiari |
| 7,309,611 | B2 | 12/2007 | DiNello et al. |
| 7,314,763 | B2 | 1/2008 | Song et al. |
| 7,371,582 | B2 | 5/2008 | Nahm et al. |
| 7,374,950 | B2 | 5/2008 | Kang et al. |
| 7,393,697 | B2 | 7/2008 | Charlton |
| 7,566,573 | B2 * | 7/2009 | Carpenter et al. ............ 436/540 |
| 7,723,124 | B2 | 5/2010 | Aberl et al. |
| 7,939,342 | B2 | 5/2011 | Song et al. |
| 2003/0190681 | A1 | 10/2003 | Shai |
| 2004/0110167 | A1 | 6/2004 | Gerdes et al. |
| 2005/0032244 | A1 | 2/2005 | Nie et al. |
| 2005/0164305 | A1 | 7/2005 | Golz et al. |
| 2005/0221386 | A1 | 10/2005 | Turner et al. |
| 2005/0227223 | A1 | 10/2005 | Miyawaki |
| 2005/0227275 | A1 | 10/2005 | Jung et al. |
| 2006/0019406 | A1 | 1/2006 | Wei et al. |
| 2006/0057608 | A1 | 3/2006 | Kaufman |
| 2006/0199278 | A1 | 9/2006 | Leclipteux et al. |
| 2006/0223192 | A1 | 10/2006 | Smith et al. |
| 2006/0263907 | A1 | 11/2006 | Zweig |
| 2007/0003992 | A1 | 1/2007 | Pentyala |
| 2007/0015290 | A1 | 1/2007 | Raj |
| 2007/0059682 | A1 | 3/2007 | Aberl et al. |
| 2007/0141564 | A1 | 6/2007 | Aberl et al. |
| 2007/0224701 | A1 | 9/2007 | Rosenstein |
| 2007/0264629 | A1 | 11/2007 | Holmes et al. |
| 2008/0032319 | A1 | 2/2008 | Nam |
| 2008/0102473 | A1 | 5/2008 | Fouquet et al. |
| 2009/0047673 | A1 | 2/2009 | Cary |
| 2009/0305231 | A1 | 12/2009 | Weidemaier et al. |
| 2010/0143891 | A1 | 6/2010 | Aberl et al. |

FOREIGN PATENT DOCUMENTS

| | | | |
|---|---|---|---|
| EP | 1489416 A1 | | 3/2003 |
| GB | 1 561 042 | * | 2/1980 |
| WO | 03073817 A2 | | 9/2003 |
| WO | 2007063326 A2 | | 6/2007 |
| WO | 2007081330 A1 | | 7/2007 |
| WO | 2007110779 A2 | | 10/2007 |

OTHER PUBLICATIONS

Sambursky et al., "The RPS Adeno Detector for Diagnosing Adenoviral Conjunctivitis", Ophthalmology, vol. 113, No. 10, pp. 1758-1764 (Oct. 2006).

Sambursky, "510-K Summary of Safety and Effectiveness" (Sep. 14, 2005).

Udeh et al., "Cost Effectiveness of a Point-of-Care Test for Adenoviral Conjunctivitis", The American Journal of the Medical Sciences, vol. 336, No. 3, pp. 254-264 (Sep. 2008).

Choi, et al., "A rapid, simple measurement of human albumin in whole blood using a fluorescence immunoassay (I)," Clinica Chimica Acta 339 (2004) pp. 147-156.

International Search Report and Written Opinion, International Application No. PCT/US2009/046848, Jun. 10, 2009.

* cited by examiner

COMBINED VISUAL/FLUORESCENCE ANALYTE DETECTION TEST

REFERENCE TO RELATED APPLICATIONS

This application claims one or more inventions which were disclosed in Provisional Application No. 61/060,258, filed Jun. 10, 2008, entitled "COMBINED VISUAL/FLUORESCENCE ANALYTE DETECTION TEST", Provisional Application No. 61/080,879, filed Jul. 15, 2008, entitled "LATERAL FLOW NUCLEIC ACID DETECTOR", Provisional Application No. 61/098,935, filed Sep. 22, 2008, entitled "IN SITU LYSIS OF CELLS IN LATERAL FLOW IMMUNOASSAYS", and Provisional Application No. 61/179,059, filed May 18, 2009, entitled "METHOD AND DEVICE FOR COMBINED DETECTION OF VIRAL AND BACTERIAL INFECTIONS". The benefit under 35 USC §119(e) of the United States provisional applications are hereby claimed, and the aforementioned applications are hereby incorporated herein by reference.

This application is also a continuation-in-part application of application Ser. No. 12/469,207, filed May 20, 2009, entitled "NANOPARTICLES IN DIAGNOSTIC TESTS", which claimed priority from Provisional Application No. 61/071,833, filed May 20, 2008, entitled "NANOPARTICLES IN DIAGNOSTIC TESTS". The aforementioned applications are hereby incorporated herein by reference.

BACKGROUND OF THE INVENTION

1. Field of the Invention

The invention pertains to the field of lateral flow immunoassays. More particularly, the invention pertains to lateral flow immunoassays with increased sensitivity due to the use of fluorescent markers.

2. Description of Related Art

Lateral flow immunoassays are a subset of antibody/antigen-based immunoassays combining various reagents and process steps in one assay strip, thus providing a sensitive and rapid means for the detection of target molecules. Lateral flow immunoassays are available for a wide area of target analytes and can be designed using sandwich or competitive test principles. Generally high molecular weight analytes with several epitopes are typically analyzed in a sandwich format whereas small molecules representing only one epitope are usually detected by means of a competitive assay. The first tests were made for human chorionic gonadotropin (hCG). Today there are commercially available tests for monitoring ovulation, detecting infectious disease organisms, analyzing drugs of abuse and measuring other analytes important to human physiology. Products have also been introduced for veterinary testing, environmental testing and product monitoring.

U.S. Pat. No. 5,714,341, herein incorporated by reference, discloses a lateral flow immunoassay for HIV specific antibodies in saliva samples. The saliva sample is diluted in a sample buffer and the lateral flow immunoassay is dipped into the diluted saliva sample.

German Patent DE 196 22 503, herein incorporated by reference, suggests the use of lateral flow immunoassays for the detection of illegal narcotics in saliva or sweat.

SUMMARY OF THE INVENTION

The present invention enhances the sensitivity of visually read lateral flow immunoassay tests by adding a small quantity of a fluorescing element, such as a fluorescing dye or fluorescing latex bead conjugates, to the initial conjugate material. When the visible spectrum test line is visible to the unaided eye, the test result is observed and recorded. However, in cases where weak positives do not give rise to a distinct visual test line or a false positive is indicated by a very faint line, a light of an appropriate spectrum, such as a UV spectrum, is cast on the test line to correctly interpret the test results. If the test is positive, the UV light will excite and fluoresce the fluorescing dye or the fluorescing latex beads which are bound in the test line to enhance the visible color at the test line. If the test is negative, there will be no fluorescing elements to excite, and there will therefore be no enhancement.

DETAILED DESCRIPTION OF THE INVENTION

Figure 1:
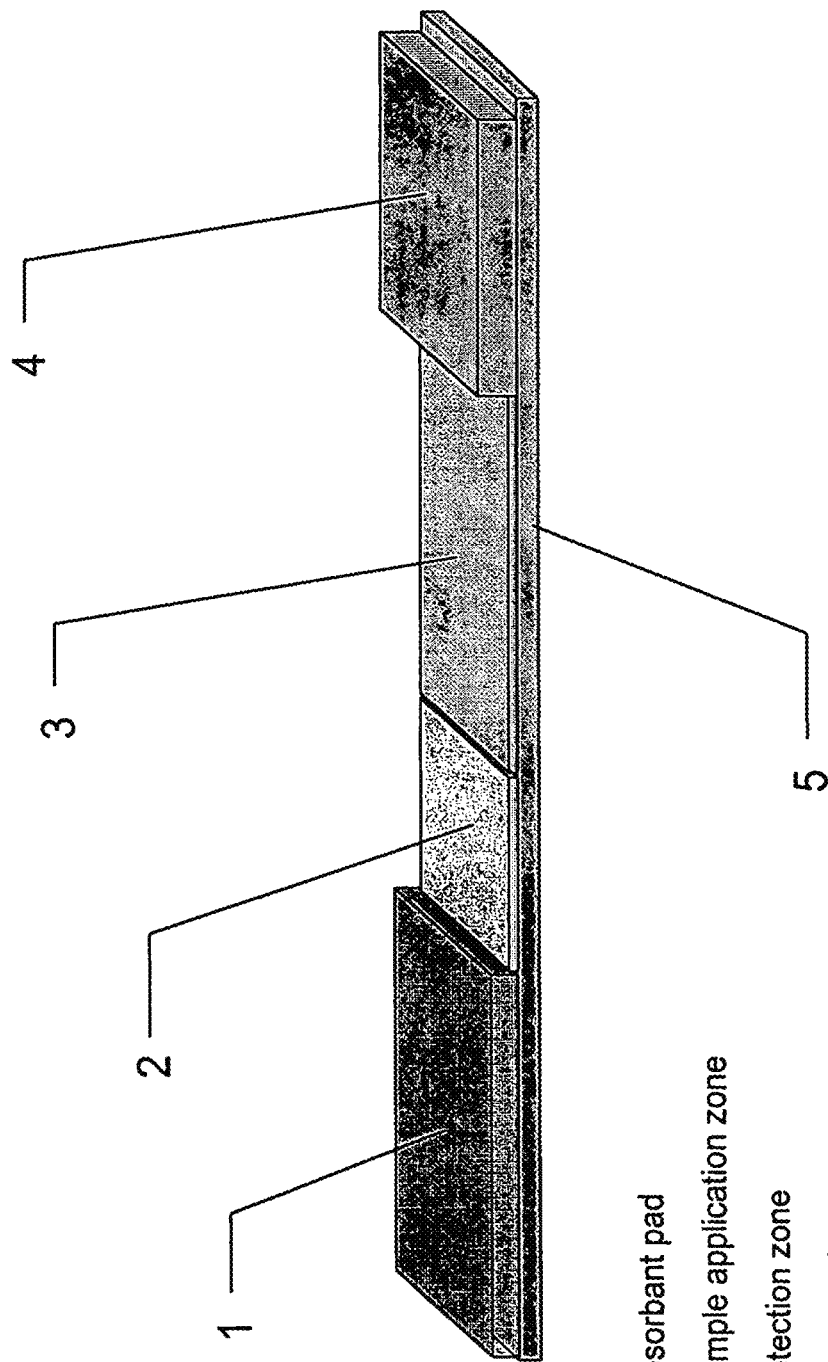
FIG. 1 shows a sample analysis device in an embodiment of the present invention.

The present invention enhances the sensitivity of visually read lateral flow immunoassay tests by adding a small quantity of at least one fluorescing element, including, but not limited to, a fluorescing dye or fluorescing latex bead conjugates, to the initial conjugate material.

In other embodiments, a fluorescent element can be "masked" by attaching the appropriate "quencher" moiety in the appropriate vicinity. When the "quencher" is excised or removed from the immediate vicinity, the fluorescence is "unmasked". This phenomenon is called Fluorescence Resonance Energy Transfer (FRET). The excision can be made part of the assay by including the appropriate excisor in the buffer or by adding an additional step in the assay format.

The methods and devices discussed herein use both a visual label and a fluorescent label together in the same assay in order to detect a target molecule. The fluorescent element is preferably used as a real time supplement to the visual indicator in a rapid result point of care sample analysis device. The fluorescent labels preferably increase the sensitivity of the test at least tenfold, without sacrificing the rapidity and simplicity of the test. The analytical tests discussed herein preferably permit a result while the patient is still being examined by the practitioner. In a preferred embodiment, the test result is obtained in under 10 minutes after applying the sample to the device, and it is preferably read at approximately 10 minutes. In samples that are highly positive, a readout of the test zone (preferably a test line) is visible within approximately 5 minutes.

The visible labels and the fluorescing elements are each coupled with at least one specific binding partner for the target molecule in the biological sample. In some preferred embodiments, the specific binding partners for the analytes in the sample are monoclonal, polyclonal or recombinant antibodies or fragments of antibodies capable of binding to a pathogen. Alternatively, the specific binding partners may also be antigens capable of binding to antibodies against a pathogen or an allergen. Other types of binding partners include, but are not limited to, bioorganic macromolecules like aptamers or receptors, nanoparticles, or nucleic acids.

Preferred targets include, but are not limited to, proteins, glycoproteins, proteoglycans, and lipoproteins. Other preferred targets include, but are not limited to, pathogens, low-molecular-weight compounds, and/or allergy-associated components. The pathogens are preferably selected from viruses, microorganisms, e.g. bacteria and parasites, e.g. amoebae or nematodes. The allergy-associated components are preferably selected from allergens and anti-allergic components. In some preferred embodiments, the target is on the surface of the cell or organism, so it is not necessary to lyse the cells to detect the target.

In some preferred embodiments, the sample is preferably a sample of body fluid. In these embodiments, the sample of body fluid is preferably taken from a body surface selected from mucosal membrane fluids (preferably of the oral, nasal, vaginal, and ocular cavities), blood, urine, tears, secretions from glands and secretions from lesions or blisters, e.g. lesions or blisters on the skin. More preferably, the sample is selected from oral, nasal, ocular, genital and rectal fluid, secretions from skin lesions or blisters, CFD (cerebral spinal fluid), and exudates.

Lateral flow devices are known, and are described in, e.g., U.S. Published Patent Application Nos. 2005/0175992 and 2007/0059682. The contents of both of these applications are incorporated herein by reference. Other lateral flow devices known in the art could alternatively be used with the systems and methods of the present invention.

U.S. Published Patent Application No. 2007/0059682, discloses detecting an analyte and a sample which can also contain an interfering subject. This publication teaches separating the analyte from the interfering substance by capturing the interfering substance on the chromatographic carrier, and detecting the analyte on the carrier separated from the interfering substance.

U.S. Published Patent Application No. 2005/0175992 discloses a method for detecting targets, such as pathogens and/or allergy-associated components, in a human body fluid where the body fluid sample is collected by a collection device, such as a swab member. The samples are transferred from the swab member to a sample analysis device, on which an analysis of the targets can occur by immunochemical or enzymatic means. The test result is capable of being displayed within a very short period of time and can be directly read out by the user. The inventions disclosed in this copending application are particularly advantageous for the diagnosis of conjunctivitis.

The chromatographic test strip shown in FIGS. 1 through 4 includes a plurality of different strip materials. The device preferably includes an absorbent pad (1), an application zone (2), a detection zone (3) and a waste zone (4). The strip materials are arranged on an adhesive plastic backing (5). The absorbent pad (1) is provided in this example for adding an elution medium in order to facilitate the transfer of the sample to the detection zone (3). US Patent Publication No. 2007/0059682, describes methods to increase specificity of lateral flow immunoassays. These methods could also be used in combination with the embodiments described herein.

Figure 2:
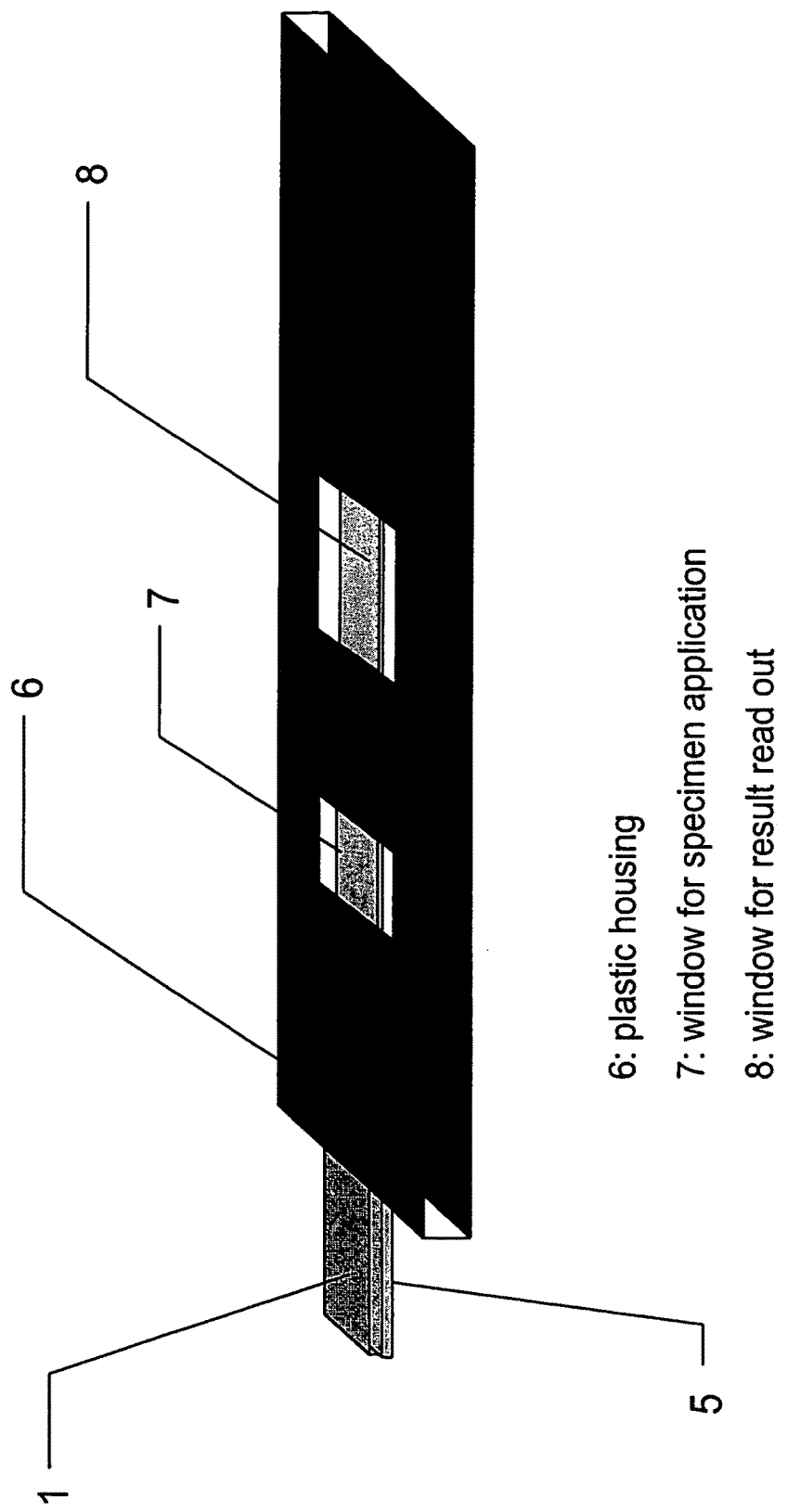
FIG. 2 shows a housing containing the strip of FIG. 1.
Figure 3:
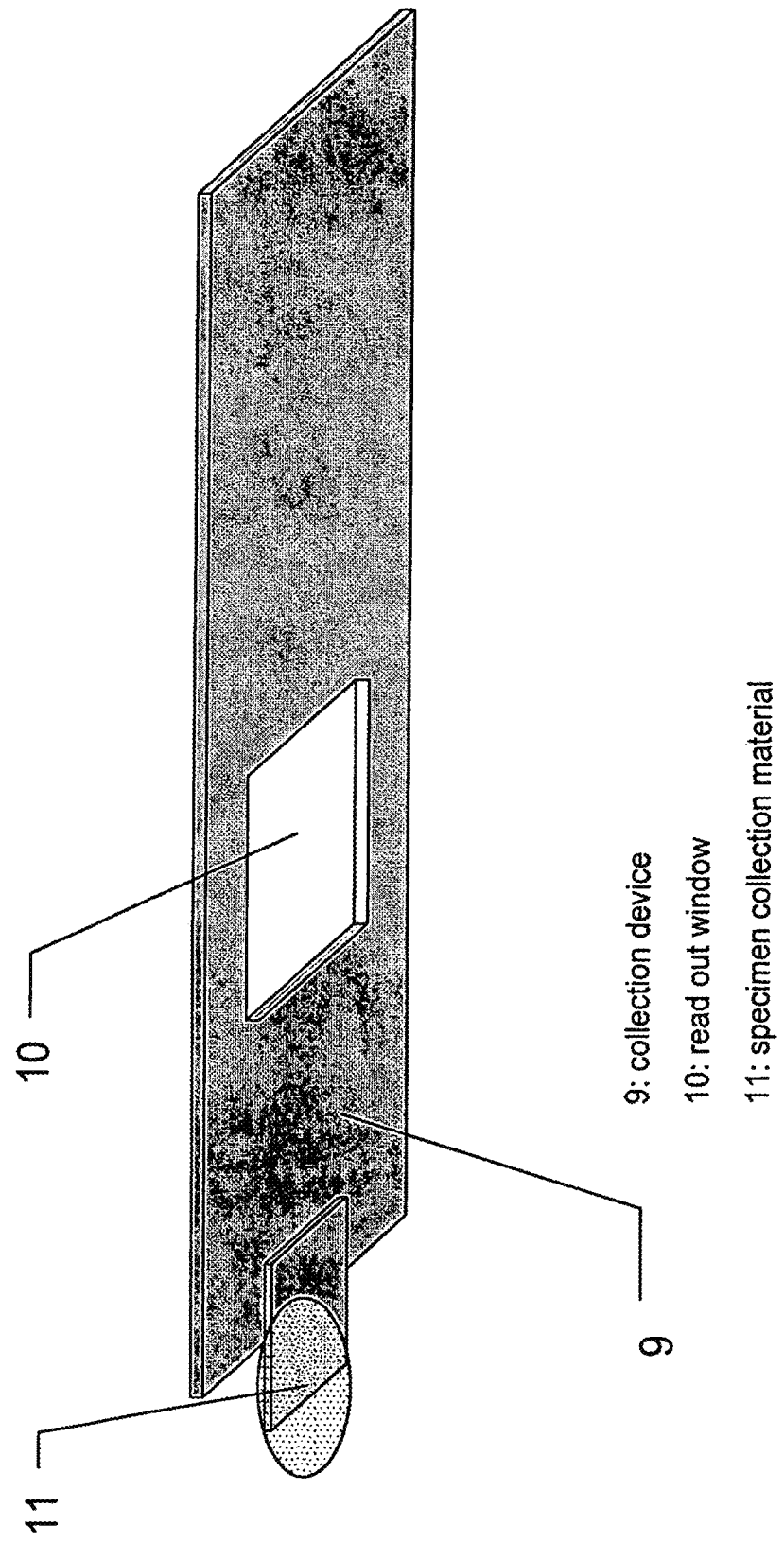
FIG. 3 shows a collection device for collecting a sample.
Figure 4:
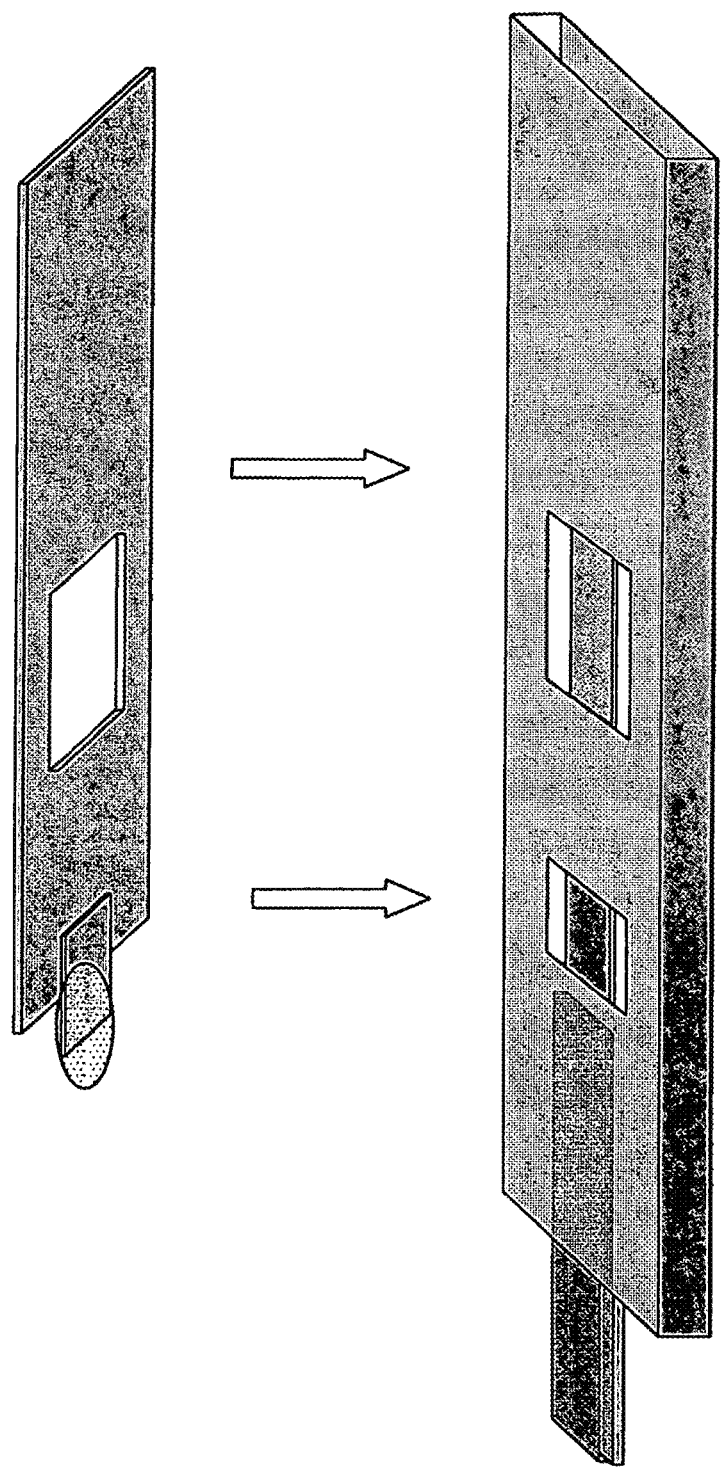
FIG. 4 shows a test kit including the sample analysis device of FIGS. 1 and 2 and the collection device of FIG. 3.

FIG. 2 shows a housing (6), which is preferably plastic, containing the strip as shown in FIG. 1. A sample application window (7) brings a collection device into contact with the strip. The test result is displayed in the read out window (8). FIG. 3 shows the collection device for collecting a sample. In one example, the collection device is a swab member. The collection device includes a body (9), which is preferably plastic, with a sample collection material (11) fixed on it and an opening (10) corresponding to a read out window when the collection device is operatively in contact with a test strip. FIG. 4 shows a test kit, which includes the sample analysis device of FIGS. 1 and 2 and the collection device of FIG. 3.

Figure 5:
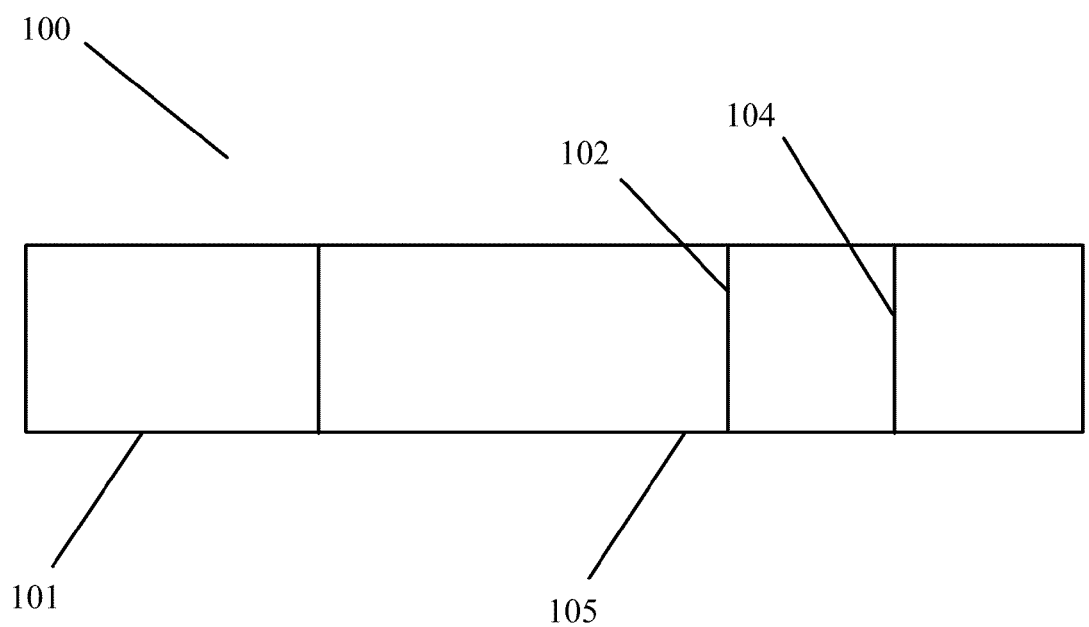
FIG. 5 shows another embodiment of a sample analysis device of the present invention.

In a method of the invention, it is possible to make use of different biochemical testing procedures to detect constituents on one or several biochemical binding reactions. In a preferred embodiment, as shown in FIG. 5, the chromatography test strip (100) includes an application zone (or sample zone) (101). The sample is applied to the application zone (101).

The test strip also includes a detection zone (105). The detection zone (105) includes at least one test zone (102), which is preferably a test line. Although only one test line is shown in the figure, multiple test lines are within the spirit of the invention. In some embodiments where there are multiple targets, the presence of each target preferably corresponds to a separate test line. In other embodiments where there are multiple targets, the presence of multiple targets may be indicated on the same test line such that the presence of more than one target has different characteristics than the presence of a single target. For example, the presence of multiple targets on the same test line may be visually indicated by a different color than the presence of each of the targets alone. The test strip (100) also preferably includes at least one control zone (104), which is preferably a control line. As shown in FIG. 5, the control zone (104) is preferably downstream of the test zone (102). However, in other embodiments, the control zone (104) may be located upstream of the test zone (102).

In the present invention, a fluorescing element is coupled to the specific binding partner for the target or targets of interest. Similarly, the visual label is also coupled to the specific binding partner for the target or targets of interest. In one embodiment, the specific binding partner is an antibody or antigen. In other embodiments, the specific binding partner includes a plurality of nanoparticles or a nucleic acid.

In embodiments where antibodies or antigens are used, the fluorescing element, coupled to the antibody or antigen as well as the general blocking agent, for example Bovine Serum Albumin (BSA), is added to the antibody or antigen coupled to the visual label. The visual label may be any label visible to the naked eye, including, but not limited to, colored particles such as colloidal gold, dyed latex beads, selenium, or carbon. In embodiments where nanoparticles are used, the nanoparticles that may be used include, but are not limited to, selenium, carbon, and colloidal gold.

The visual tags are also coated with fluorescing elements. In one embodiment, the fluorescing element is a fluorescing dye. Alternatively, a mixture of preferably colorless fluorescing latex bead conjugates are mixed with colloidal gold (a visible spectrum) conjugates, or conjugates producing a visible read test line, in lateral flow immunoassays to enhance sensitivity of the assay and to aid in visually reading true positives and true negatives.

In a preferred embodiment, visually red particles, such as colloidal gold or red dyed latex beads, are conjugated with the antibody or antigen specific to the target and the antibody or antigen is also coupled to a fluorescing dye. The conjugated or coupled antibody or antigens are blocked with a mixture of a general blocking agent and a fluorescing dye blocking agent. In some embodiments, the blocking agent is bovine serum albumin.

In another embodiment, red colored colloidal gold or red dyed latex bead conjugates and colorless fluorescent latex beads that fluoresce to produce a red color under UV excitation are used. In this embodiment, the red colored colloidal gold or red dyed latex bead conjugates are conjugated with the antibody or antigen specific to the target and the antibody or antigen is also coupled to the colorless fluorescent latex beads. The conjugated or coupled antibody or antigens are blocked with a mixture of a general blocking agent and a fluorescent latex bead blocking agent. In some embodiments, the blocking agent is bovine serum albumin.

In both the embodiments with fluorescing dye and the embodiments with colorless fluorescent latex beads, when the test is conducted to determine the presence of an analyte in a sample, if the tester sees a visibly distinct red test result, such as a test line (120), initially, the tester would record the result as a positive. If a distinct test line is not visible, or if the test line appears as a shadow or a faint line (150), then the tester would shine a fluorescent light on the test line. The weak visible spectrum positives that were not distinctly discemable before would now fluoresce in the red color (130) and the red test line can be distinctly visualized.

While the embodiments discussed above utilize mixing colloidal gold (or red dyed latex beads) with a fluorescing dye or colorless fluorescent latex bead conjugates that fluoresce to produce a red color to maintain the color red associated with the test line, in other embodiments, any color may be used for the dyed latex beads, the fluorescing dye, and/or the fluorescing beads. Similarly, the same color does not necessarily need to be maintained, so that the fluorescing dye or the fluorescing beads when excited can have a different color than the gold labeled particles or the dyed latex beads. Other colorless fluorescent beads which can be excited at other wavelengths including those in the visible spectrum and those that will fluoresce to emit colors of the visible spectrum other than the red color mentioned above can also be used in the present inventions to achieve greater sensitivity with the fluorescent beads.

One of the preferred embodiments is made by coupling the specific binding partner, for example an antibody or antigen, mixed with fluorescing dye and then conjugating the coupled antibody or antigen to the colloidal gold or red dyed latex beads. Another preferred embodiment is made by adding 1% by volume of colorless UV fluorescing latex bead conjugates that fluoresce to produce a red color to the optimum quantity of the colloidal gold (visible spectrum) conjugates. The 1% colorless fluorescing latex beads enable visual reading of the test line with a minimum of a tenfold increase in sensitivity at the lower limit of detection of the visible spectrum labeled conjugate.

The UV fluorescing beads fluoresce with varying luminosity depending on the wavelength of the excitation source. A greenish lower luminosity is excited with 395 nm light. The "gold" colored band with a higher luminosity is excited with 365 nm light. It is well within the skill of those in the art to choose a color and a light source to achieve a test result readily visible under a fluorescent light source.

The fluorescing latex beads are preferably colorless under ambient light so as to not interfere with the reading of a strong positive result. However, it will be readily appreciated that the fluorescing latex beads can alternatively be lightly colored. The fluorescing latex beads typically have a diameter of 1 to 500 nm, preferably 20 to 400 nm.

While the fluorescing latex beads or the fluorescing dye preferably fluoresce at ultraviolet light wavelengths (10 nm to 400 nm), any system where the beads or the dye will be excited and fluoresce at other wavelengths could also be utilized in the present invention. For example, in some embodiments, wavelengths in the range of 480 nm to 490 nm are used. Alternative wavelengths within the spirit of the present invention include, but are not limited to, all visible (400 nm to 700 nm) and infrared (750 nm and 100 Mm) spectra.

The fluorescing latex beads should be mobile to be transported along the test strip until captured in the test zone and/or the control zone. Suitable examples of beads that can be used in the present invention include carboxylated latex beads, latex beads that can couple to proteins passively and beads that can be coupled to proteins by other chemistries.

The fluorescing latex beads are preferably mobile on the immunoassay test strip under the action of a suitable buffer, which permits the use of small volumes of analyte, but in the case of a body fluid such as urine, the body fluid itself may cause transport of the fluorescing latex bead conjugates, as well as the gold label conjugates, along the test strip.

In a visually read lateral flow immunoassay, the visible luminosity of the visually read test line (102) is determined by the number of gold label particles that accumulate at the test line. In tests which may be near the set lower limit of the visible read test line (102), the sensitivity of the visually read lateral flow immunoassay test is enhanced by adding a small quantity of the fluorescing element, for example a fluorescing dye or fluorescing bead conjugates, to the initial conjugate material (such as gold labeled conjugate material or dyed latex bead conjugate material) and can be excited with a fluorescent light source, for example a small UV light, to provide an aid in clarifying a true positive versus a true negative test result.

In embodiments using a mixture of fluorescing beads with the visible dyed conjugate particles, the fluorescing latex beads which are used in the present invention are preferably colorless in the visible spectrum, and fluoresce under UV light. These latex beads are conjugated to an antibody or other binding partner which reacts with a capture analyte at the test line (102) in the same manner as the gold labeled particles, so that both the fluorescing latex beads and the gold labeled particles accumulate at the test line (102). A suitable amount of the UV fluorescing latex bead conjugates is preferably 0.1% to 10% by volume, based on the volume of the visible colloidal gold or dyed latex bead conjugates, and preferably is about 1% by volume of the visible colloidal gold or dyed latex bead conjugates. When the visible spectrum test line (102) is visibly present, the test result is observed and recorded, and no ultraviolet light excitation is required. In the case of a weak positive result that does not give rise to a distinct visual test line (102), a UV spectrum light is cast on the test line to excite and fluoresce the fluorescent latex beads to indicate the presence of the fluorescent latex beads bound in the test line (102).

Figure 6:
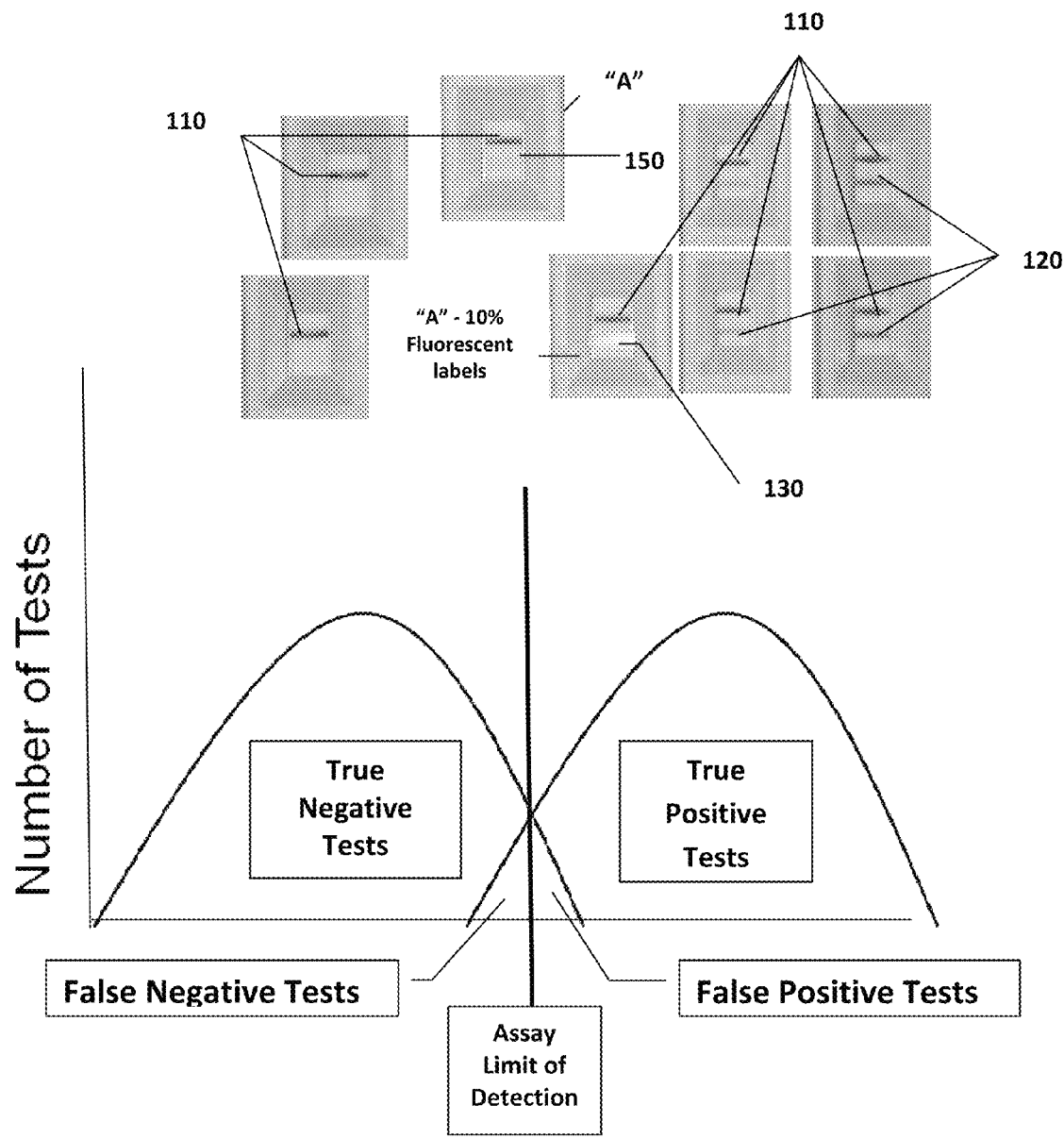
FIG. 6 shows examples of test results and how using fluorescence enhances the ability to interpret the test result for weak positives.

Referring to FIG. 6, visually read assays rely on the binding and the subsequent accumulation of visible labels at the predetermined test line (102). The limit of detection for a visibly read assay is set by controlling the number of accumulated visible labels to a number of labels which is less than can be seen with the unaided eye when the analyte present is at the desired limit of detection. As shown in the graph, there is a spectrum of the level of analyte in a particular sample, which will affect the reading of the test. When the number of labels is less than the limit of detection, the test line (120) will not be visible and the test result is interpreted as a negative test.

A practical problem occurs when the analyte present is at or near the limit of detection of the assay. In this instance, the test line (150) will appear faintly as in graphic "A". For the tests performed where the amount of analyte is somewhere around the assay limit of detection, there is an overlap between the results obtained for true positive and true negative tests. This condition results in interpretations of the assay which may be either a false negative (for true positive tests that are not detectable by the unaided eye) or a false positive (for true negatives that result in a very faint line visible to the naked eye). A control line (110) is preferably used in all tests to show that the test is working.

Figure 7:
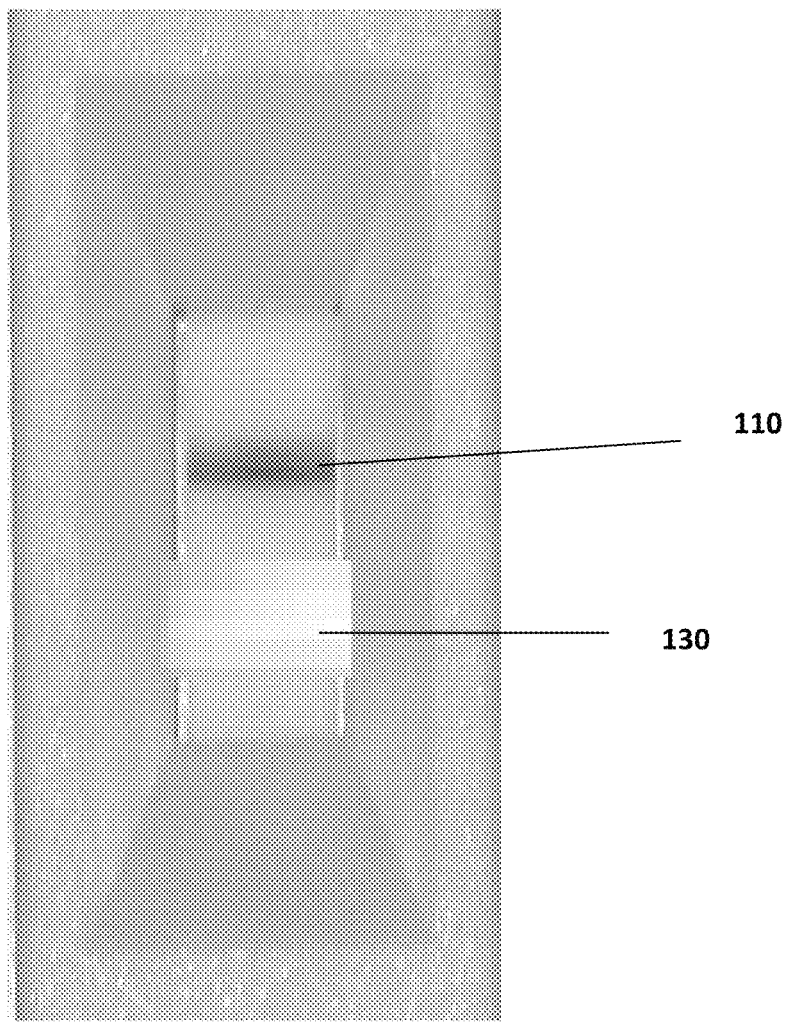
FIG. 7 shows a close up view of a positive fluorescent test result for the weakly positive visual test shown in FIG. 6.

In one preferred embodiment, the number of false test readings can be reduced by combining 10% fluorescent labels with the visible labels. FIG. 7 shows a close up view of the "A-10% fluorescent labels" test result. The fluorescent labels are preferably a fluorescing dye or fluorescing bead conjugates. When the analyte is at or near the limit of detection and the visible label is faint, the fluorescent labels will produce a visible signal when excited by a 490 nm diode laser. The visible line (130) of the fluorescing labels will confirm the test as a positive test (refer to graphic "A-10% fluorescent labels").

Figure 8:
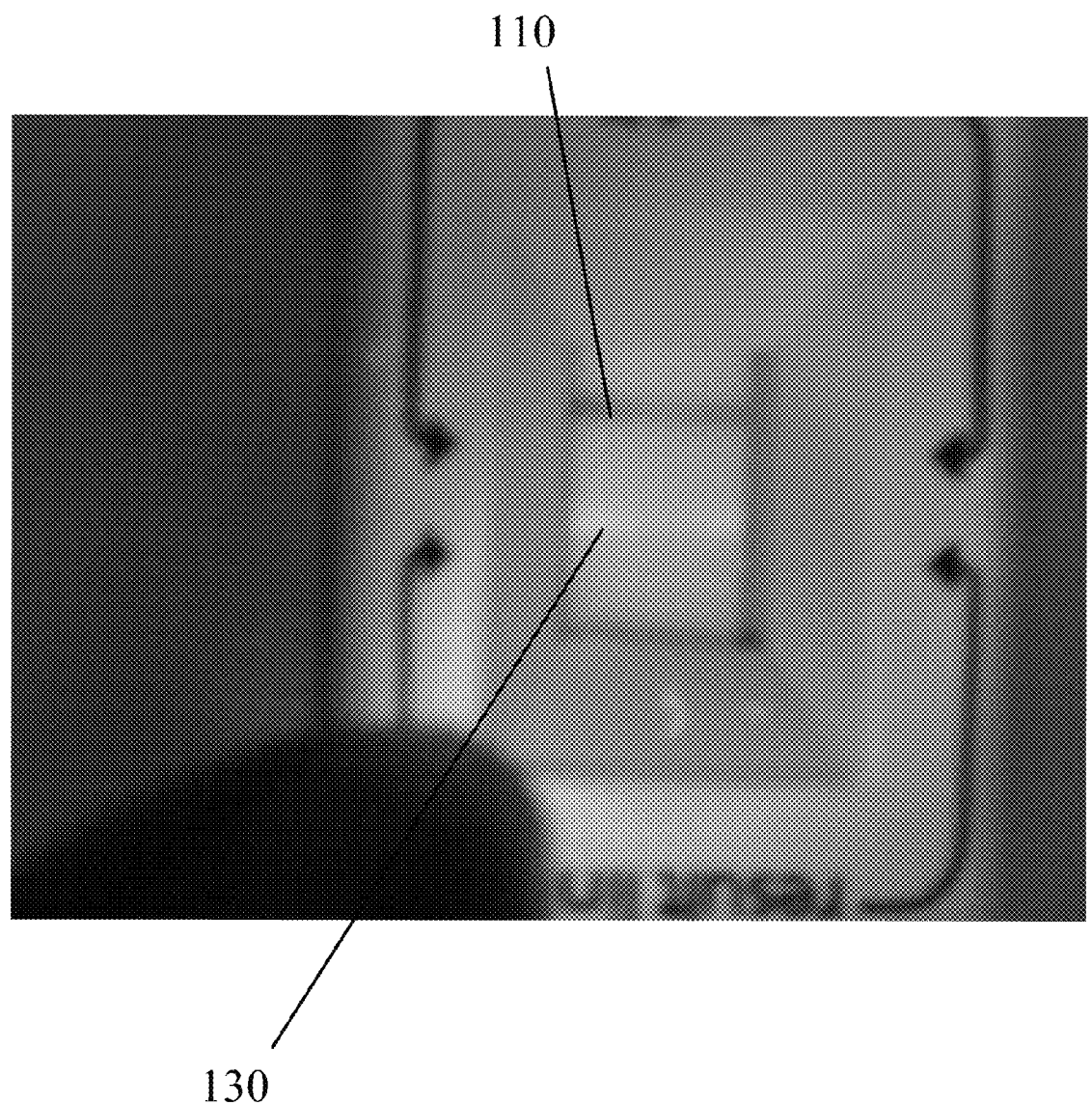
FIG. 8 shows a close up view of another positive fluorescent test result for a weakly positive visual test.

FIG. 8 shows a close-up view of another example of a positive test, where the fluorescent line (130) is shown.

In a preferred embodiment, the present invention provides for the reduction of interfering substances that might be present in the sample to be tested. Since an interfering substance, e.g. a human anti-mouse antibody (HAMA), may also be capable of forming a complex with the labeled, non-immobilized reagent of the reagent zone and the immobilized binding partner of the detection zone, thus indicating a positive test result in the immunoassay, the carrier may further include at least one capturing zone. Each capturing zone contains an immobilized capturing reagent specifically binding to a certain interfering substance, thereby immobilizing the interfering substance in the capturing zone. As the capturing zone is separated from the detection zone by space, and the sample starts to migrate over the reagent zone and the capturing zone before reaching the carrier's detection zone, the method allows a separation of the interfering substance or substances from the analyte or analytes of interest. Preferably, the capturing zone is located between the reagent zone and the detection zone. However, the capturing zone may also be located between the application zone and the reagent zone.

In some preferred embodiments, the sample that has been collected is not lysed prior to collection and transfer to the sample analysis device. This decreases the number of steps needed to collect and prepare the sample for analysis. Following sample loading, the sample traveling with the transport liquid (buffer) will encounter a lysis or lysing agent. The lysis agent will have preferably been pre-loaded and dried onto the test strip and is eluted by the transport liquid. The initially dried lysis agent is preferably localized between the sample application zone and a conjugate zone. The lysis agent is preferably soluble in the sample transport liquid, and the lysis agent is solubilized and activated upon contact with the sample transport liquid. The sample transport liquid then contains both lysis agent in solution or suspension and sample components in suspension. Any lysis-susceptible components in a sample, then being exposed in suspension to the lysis agent, are themselves lysed in situ. The running buffer then carries the analyte, including any lysis-freed components, to a detection zone.

The location where the lysis agent is pre-loaded and dried can be varied as needed. In order to maximize the time that the sample has to interact with the lysis agent as well as to minimize the amount of lysis agent reaching the detection zone, the dried lysis agent may be located in or just downstream of the sample application zone. Or, in order to minimize the distance along which the lysis product must travel before reaching the conjugate zone, the dried lysis agent may be located closer to the conjugate zone.

In some embodiments, the present invention provides a lateral flow assay that uses the combined visual/fluorescence detection test to help differentiate viral and bacterial infections. A combined point of care diagnostic device tests markers for both viral and bacterial infection, and can effectively assist in the rapid differentiation of viral and bacterial infections, for example at the outpatient office or during an urgent care visit. This ability can dramatically reduce health care costs by limiting misdiagnosis and the subsequent overuse of antibiotics. Such a practice may limit antibiotic allergies, adverse events, and antibiotic resistance. The rapid result obtained from the test also permits a result while the patient is still being examined by the practitioner.

In one preferred embodiment, the marker for viral infection is MxA and the marker for bacterial infection is C-reactive protein (CRP). High MxA protein levels are strongly correlated with systemic viral infection and increased CRP is more associated with bacterial infections. The present invention includes a rapid infectious screening test for identifying MxA and CRP in samples. MxA is present in leukocytes (white blood cells). Therefore, the sample can be taken anywhere leukocytes are available, for example in a peripheral blood sample, nasopharyngeal aspirates, tears, spinal fluid, and middle ear aspirates.

In other embodiments, other markers for viral infection and/or bacterial infection may be used. For example, approximately 12% of host genes alter their expression after Lymphocytic Choriomeningitis Virus (LCMV) infection, and a subset of these genes can discriminate between virulent and nonvirulent LCMV infection. Major transcription changes have been given preliminary confirmation by quantitative PCR and protein studies and are potentially valuable candidates as biomarkers for arenavirus disease. Other markers for bacterial infection include, but are not limited to, procalcitonin, urinary trypsin inhibitor (uTi), lipopolysaccharide, IL-1, IL-6, IL-8, IL-10, ESR and an elevated WBC count (increased bands), Lactate, Troponin, vascular endothelial growth factor, platelet derived growth factor, cortisol, proadrenomedullin, macrophage migratory inhibitory marker, activated protein C, CD 4, 8, 13, 14, or 64, caspase, placenta derived growth factor, calcitonin gene-related peptide, high mobility group 1, copeptin, naturietic peptides, lipopolysaccharide binding protein, tumor necrosis factor alpha, circulating endothelial progenitor cells, complement 3a, and triggering receptor expresssed on myeloid cells (trem-1).

In one embodiment, the infections being distinguished are respiratory infections. In other embodiments, other types of infections, which can be bacterial or viral, are differentiated using the system of the present invention. Some examples include, but are not limited to, encephalitis, meningitis, gastroenteritis, febrile respiratory illness (including bronchitis, pharyngitis, pneumonia), sinusitis, otitis media, urinary tract infections, and conjunctivitis.

EXAMPLE 1

Red dyed 320 nm latex beads are coupled to 50 ug/ml AD 51 Adeno Hexon specific monoclonal antibody and 10 ug/ml of AD 51 Adeno Hexon specific monoclonal antibody is conjugated to the Dylight 405 fluorescing dye. The conjugated beads are then blocked with 2% BSA containing 1 mg/ml Dylight 405 coupled BSA. The visibly red latex beads conjugate also fluoresces under the UV light. This conjugate is used in a conjugate zone of the lateral flow test strip and serves as the visual (and fluorescing) tag in an Adeno Detector™ lateral flow test.

EXAMPLE 2

Colloidal gold of 20 to 40 nm size conjugated to AD51 Adeno Hexon specific monoclonal antibody is mixed with colorless fluorescing latex beads conjugated to the same AD51 monoclonal antibody. This mixture of visibly red colloidal gold conjugate and the colorless fluorescing latex beads is impregnated as the visual tag in the conjugate zone of an Adeno Detector™ lateral flow strip.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of running an assay on a sample, comprising the steps of:
   a) transferring the sample to a sample analysis device, wherein the sample analysis device comprises a plurality of labels visible to an unaided eye and a plurality of fluorescing elements, wherein the labels and the fluorescing elements are each coupled with at least one specific binding partner for a target in the sample; and
   b) analyzing the sample for a presence of at least one target, comprising the substeps of,
      i) determining if a label is visible to the unaided eye at a test zone of the sample analysis device; and
      ii) if a visibility of the label is indeterminate, casting a fluorescent light source on the test zone to determine whether a result is positive using fluorescence.

2. The method of claim 1, wherein the specific binding partner comprises an antibody or an antigen.

3. The method of claim 1, further comprising, before step a), the step of collecting the sample.

4. The method of claim 1, wherein substep ii) enhances a sensitivity of the method at least tenfold compared to a method that only uses a visual-label to determine a result.

5. The method of claim 1, wherein step b) is performed within 10 minutes of transferring the sample to the sample analysis device.

6. The method of claim 1, wherein step b) is performed within 10 minutes of transferring the sample to the sample analysis device.

7. The method of claim 1, wherein the labels visual to the unaided eye are selected from the group consisting of a plurality of colloidal gold particles; a plurality of dyed latex beads; a plurality of selenium particles; and a plurality of carbon particles.

8. The method of claim 1, wherein the fluorescing element is a fluorescing dye.

9. The method of claim 1, wherein the fluorescing element comprises a plurality of colorless fluorescing latex beads.

10. The method of claim 9, wherein a volume of the fluorescing latex beads coupled with the specific binding partner is approximately 0.1% to 10% of a volume of the labels visible to the unaided eye coupled with the specific binding partner.

11. The method of claim 1, wherein the labels visible to the unaided eye and the fluorescing elements are blocked with a blocking agent.

12. The method of claim 11, wherein the blocking agent is bovine serum albumin.

13. The method of claim 1, wherein the sample analysis device comprises at least two test lines to determine a presence of at least two targets.

14. The method of claim 1, wherein the sample analysis device comprises a single test line to determine a presence of at least two targets.

15. The method of claim 1, wherein a visible color of the label visible to the unaided eye is the same as a fluorescing color of the fluorescing element.

16. The method of claim 1, wherein a visible color of the label visible to the unaided eye is different than a fluorescing color of the fluorescing element.

17. The method of claim 1, wherein the sample analysis device is a lateral flow chromatographic test strip and further comprises:
   a) an application zone for applying a sample to the sample analysis device;
   b) a detection zone for detecting the analyte, wherein the detection zone is laterally downstream from the application zone.

18. The method of claim 1, wherein the labels visible to an unaided eye and the plurality of fluorescing elements are coupled to the same specific binding partner for the target.

19. The method of claim 1, wherein the at least one specific binding partner comprises a mixture of at the least one specific binding partner coupled to the plurality of labels visible to an unaided eye and the at least one specific binding partner coupled to the plurality of fluorescing elements.

* * * * *

UNITED STATES PATENT AND TRADEMARK OFFICE
CERTIFICATE OF CORRECTION

PATENT NO. : 8,470,608 B2  Page 1 of 1
APPLICATION NO. : 12/481631
DATED : June 25, 2013
INVENTOR(S) : Babu et al.

It is certified that error appears in the above-identified patent and that said Letters Patent is hereby corrected as shown below:

In the Claims

Claim 5 (Column 9, line 42): replace "visual-label," with "visual label"

Claim 19 (Column 10, line 44): replace "mixture of at the least one" with "mixture of the at least one"

Signed and Sealed this
Seventeenth Day of September, 2013

Teresa Stanek Rea
*Deputy Director of the United States Patent and Trademark Office*